(12) United States Patent
Yoo et al.

(10) Patent No.: US 12,724,015 B2
(45) **Date of Patent: *Sep. 1, 2026**

(54) PREDICTION OF RESEARCH OCTANE NUMBER USING A CONSTANT VOLUME COMBUSTION CHAMBER

(71) Applicant: PRECISION ANALYZER COMPANY, LP, Wilmington, DE (US)

(72) Inventors: Kwang Hee Yoo, Houston, TX (US); Michael Brosseau, Houston, TX (US); Thomas Herold, Boxberg-Uiffingen (DE)

(73) Assignee: PRECISION ANALYZER COMPANY L.P., Wilmington, DE (US)

( * ) Notice: Subject to any disclaimer, the term of this patent is extended or adjusted under 35 U.S.C. 154(b) by 300 days.

This patent is subject to a terminal disclaimer.

(21) Appl. No.: 18/479,518

(22) Filed: Oct. 2, 2023

(65) Prior Publication Data

US 2024/0133853 A1 Apr. 25, 2024

Related U.S. Application Data

(60) Provisional application No. 63/380,005, filed on Oct. 18, 2022.

(51) Int. Cl.

| | |
|---|---|
| ***G01N 33/00*** | (2006.01) |
| ***G01N 7/06*** | (2006.01) |
| ***G01N 33/24*** | (2006.01) |

(52) U.S. Cl.
CPC ........... *G01N 33/0016* (2013.01); *G01N 7/06* (2013.01); *G01N 33/0026* (2013.01); *G01N 33/241* (2013.01)

(58) Field of Classification Search
CPC .. G01N 33/0016; G01N 7/06; G01N 33/0026; G01N 33/241; G01N 33/2829;
(Continued)

(56) References Cited

U.S. PATENT DOCUMENTS 7,529,616 B2 * 5/2009 Bizub ................ G01N 33/2829 701/111
7,925,449 B2 4/2011 Lutnick et al.
(Continued)

OTHER PUBLICATIONS

Nimal Naser, S. Mani Sarathy, Suk Ho Chung, Estimating fuel octane numbers from homogeneous gas-phase ignition delay times, Combustion and Flame, vol. 188, (2018), pp. 307-323.
(Continued)

*Primary Examiner* — Francis C Gray
(74) *Attorney, Agent, or Firm* — Troutman Pepper Locke LLP

(57) ABSTRACT

A device may include a memory storing instructions and a processor configured to execute the instructions to obtain a research octane number for a sample; perform a combustion test for the sample in a constant volume combustion chamber; and record, at time points during the combustion test, pressure values. The processor may be further configured to calculate values for one or more pressure parameters for the sample based on the pressure values; generate a research octane number function for the constant volume combustion chamber based on the determined research octane number and the calculated values for the one or more pressure parameters; and use the generated research octane number function to determine research octane numbers for samples using the constant volume combustion chamber.

20 Claims, 9 Drawing Sheets

(58) Field of Classification Search
CPC ....... G01N 31/12; G06N 20/00; G01M 15/08; G01M 15/048; G01M 15/05
See application file for complete search history.

(56) References Cited

U.S. PATENT DOCUMENTS

| | | | | |
|---|---|---|---|---|
| 8,506,656 | B1 | 8/2013 | Turocy | |
| 8,646,312 | B2 | 2/2014 | Ritz et al. | |
| 8,930,149 | B1 | 1/2015 | Koseoglu | |
| 8,999,012 | B2 | 4/2015 | Kelly | |
| 9,476,867 | B2 | 10/2016 | Lutnick et al. | |
| 9,823,233 | B2 | 11/2017 | Michaelis | |
| 10,168,311 | B2 | 1/2019 | Lutnick et al. | |
| 10,294,436 | B2 | 5/2019 | Orlebar et al. | |
| 10,808,195 | B2 | 10/2020 | Abdul-Manan et al. | |
| 10,947,468 | B2 | 3/2021 | Ali et al. | |
| 10,948,475 | B2 | 3/2021 | Lutnick et al. | |
| 11,119,088 | B2 | 9/2021 | Munsif | |
| 2007/0239345 | A1 | 10/2007 | Bizub | |
| 2008/0213914 | A1* | 9/2008 | Ritz | G01N 31/12 436/139 |
| 2013/0340502 | A1* | 12/2013 | Maruta | G01N 33/28 73/35.02 |
| 2016/0326976 | A1* | 11/2016 | Huber | F02D 35/027 |
| 2018/0355265 | A1 | 12/2018 | Price et al. | |
| 2020/0292518 | A1 | 9/2020 | Munsif | |
| 2021/0208125 | A1 | 7/2021 | Lutnick et al. | |
| 2021/0311013 | A1 | 10/2021 | Fogarty et al. | |

OTHER PUBLICATIONS

Jon Luecke, Bradley T. Zigler, Rapid prediction of fuel research octane number and octane sensitivity using the AFIDA constant-volume combustion chamber, Fuel, vol. 301, (2021) 120969, 12 pages.

ASTM D7668, “Standard Test Method for Determination of Derived Cetane Number (DCN) of Diesel Fuel Oils-Ignition Delay and Combustion Delay Using a Constant Volume Combustion Chamber Method”, Copyright by ASTM Int'l (all rights reserved); Tue May 4, 16:05:46 EDT 2021, 13 pages.†

Naser N, Yang S, Kalghatgi G, Chung S. Relating the octane numbers of fuels to ignition delay times measured in an ignition quality tester (IQT). Fuel 2017; 187:117-127, 11 pages.†

* cited by examiner
† cited by third party

PREDICTION OF RESEARCH OCTANE NUMBER USING A CONSTANT VOLUME COMBUSTION CHAMBER

CROSS-REFERENCE TO RELATED APPLICATION

The present application is a non-provisional of and claims priority to U.S. Provisional Patent Application No. 63/380,005, filed on Oct. 18, 2022, the entirety of which is hereby incorporated by reference herein.

BACKGROUND INFORMATION

Hydrocarbon products, such as petroleum and biomass, are used as a source of fuel in combustion engines. Different types of hydrocarbon fuels have different constituents that exhibit different combustion characteristics. Thus, different constituents may affect the performance of a hydrocarbon fuel. A combustion test may be performed on a hydrocarbon fuel sample to determine various properties of the sample. Performing a combustion test and characterizing the results of the combustion test may pose various challenges.

DETAILED DESCRIPTION OF PREFERRED EMBODIMENTS

Figure 1:
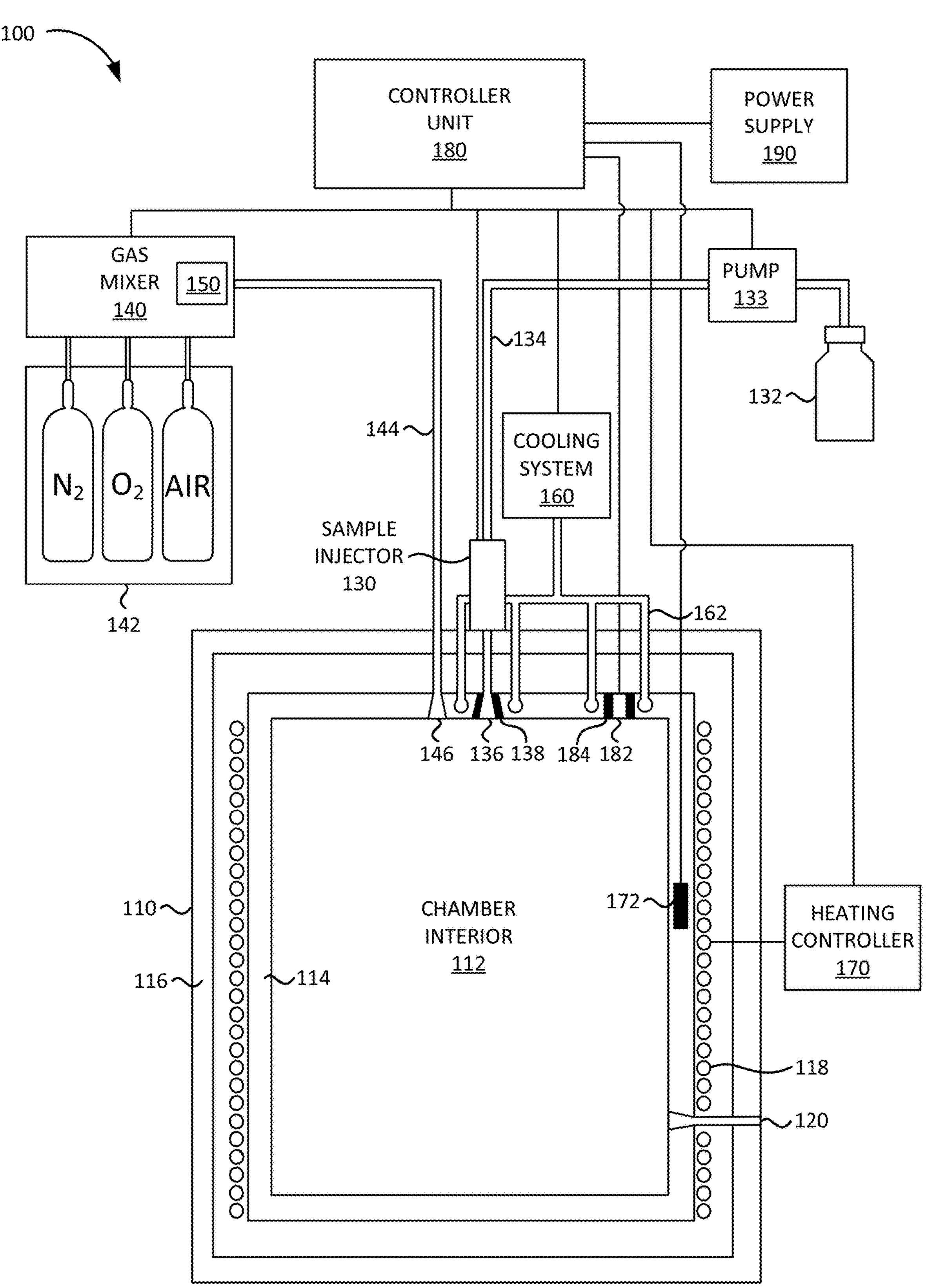
FIG. 1 illustrates a constant volume combustion chamber system according to an implementation described herein.

The following detailed description refers to the accompanying drawings. The same reference numbers in different drawings identify the same or similar elements.

Research octane number (RON) is the numerical rating of knock resistance for spark-ignition engine fuels. Knock resistance is a fuel's ability to not self-ignite and burn in an uncontrolled manner while the fuel is being compressed. A RON may be determined for a fuel by running the fuel in a test engine under controlled conditions and comparing the results with the results obtained from a reference mixture of iso-octane and n-heptane (referred to as a primary reference fuel (PRF) blend). In comparison to a Motor Octane Number (MON), another measure of knock resistance, a RON is measured at lower engine speeds (e.g., 600 revolutions per minute (rpm) vs. 900 rpm for MON, etc.), at lower temperatures (e.g., without preheating the fuel mixture, etc.), and/or without using variable ignition timing. The combustion test may be performed in a standardized single-cylinder Cooperative Fuel Research (CFR) engine. The use of such an engine for performing combustion tests has many drawbacks, such as the requirements for a large volume of fuel per test, a highly trained operator, and a large space for the engine itself. Furthermore, the high complexity of the test method that uses a CFR engine exhibits limited repeatability and reproducibility of the measurements, resulting in great expense in formulating standardized fuels.

Instead of using a single-cylinder CFR engine, a combustion test may be performed using a constant volume combustion chamber. A constant volume combustion chamber may use pressure and temperature to create an autoignition event to measure RON. A constant volume combustion chamber may be used to obtain pressure versus time data and the pressure versus time data may be used to estimate the RON for a sample.

Implementations described herein relate to determining a RON for a fuel sample using a constant volume combustion chamber and a research octane number function based on at least one pressure parameter. For example, a controller unit for a constant volume combustion chamber may be configured to obtain a RON for a sample, perform a combustion test for the sample in the constant volume combustion chamber, record pressure versus time data for the sample, and calculate a set of values for one or more pressure parameters for the sample based on the pressure versus time data. The set of values may then be used to generate a RON function for the constant volume combustion chamber based on the obtained RON and the calculated set of pressure parameter values. The process may be repeated for a set of different samples with different RONs in order to generate an accurate RON function for the combustion chamber.

The RON function may be used to determine a RON for samples for which a RON has not previously been determined. For example, the controller unit may perform a combustion test on a sample in the constant volume combustion chamber and calculate a set of pressure parameter values based on the combustion test. The controller unit may then determine a RON for the sample using the RON function and the set of pressure parameter values as inputs into the RON function.

The pressure parameters may include a minimum pressure parameter; a maximum pressure parameter; a maximum pressure rise rate, corresponding to a maximum first derivative of pressure; a maximum low temperature pressure rise rate, corresponding to a maximum first derivative of pressure during low temperature heat release (LTHR); a maximum pressure rise rate ignition delay, corresponding to a time at which the first derivative of pressure reaches a maximum level and representing a maximum heat release rate point; a low temperature ignition delay, corresponding to a time at which the first derivative of pressure reaches a particular threshold value during LTHR, representing the LTHR start; a high temperature ignition delay, corresponding to a time at which the third derivative of pressure reaches a maximum level before the maximum first derivative of pressure occurs, representing the high temperature heat release (HTHR) start; and/or other types of parameters that may be derived from pressure versus time data. The implementations described herein may provide better prediction of a RON for fuels, such as high alcohol content fuels.

FIG. 1 illustrates a constant volume combustion chamber system 100 according to an implementation described herein. As shown in FIG. 1, constant volume combustion chamber system 100 may include a constant volume combustion chamber 110, a sample injector 130, a sample container 132, a pump 133, a sample conduit 134, a gas mixer 140, gas cylinders 142, a gas conduit 144, a cooling system 160, cooling system conduits 162, a heating controller 170, a controller unit 180, and a power supply 190.

Constant volume combustion chamber 110 may include a chamber interior 112, inner walls 114, outer walls 116, a heating element 118, an exhaust port 120, sample injector nozzle 136, injector cooling jacket 138, gas conduit nozzle 146, temperature sensor 172, pressure sensor 182, and pressure sensor cooling jacket 184.

Inner walls 114 may enclose chamber interior 112 and outer walls 116 may protect and insulate inner walls 114 and chamber interior 112 from the outside environment. Inner walls 114 and outer walls 116 may enclose heating element 118. Heating element 118 may include a resistive heating element and/or another type of heating element to enable heating controller 170 to raise the temperature of chamber interior 112 to a particular temperature. Exhaust port 120 may enable gases to be removed from chamber interior 112 after a combustion test is completed.

Sample injector nozzle 136 may connect sample conduit 134 to chamber interior 112 and inject a sample into chamber interior 112 for a combustion test. Injector cooling jacket 138 may thermally insulate sample injector nozzle 136 from inner walls 114 to ensure that the sample being injected into chamber interior 112 does not prematurely rise in temperature and protect sample injector 130 and sample injector nozzle 136 from high temperatures. Gas conduit nozzle 146 may connect gas conduit 144 to chamber interior 112 and inject a gas mixture into chamber interior 112 for a combustion test.

Gas mixer 140 may include oxygen sensor 150. Oxygen sensor 150 may measure the oxygen content of the gas mixture in gas conduit 144 exiting gas mixer 140. Gas mixer 140 may adjust the content of gas mixture based on information received from oxygen sensor 150 and based on a gas mixture specification received from controller unit 180. Temperature sensor 172 may include a thermocouple, a resistance temperature sensor, a thermistor temperature sensor, a semiconductor temperature sensor, and/or another type of temperature sensor. Temperature sensor 172 may measure the temperature of chamber interior 112 and provide the measured temperature to controller unit 180 and/or heating controller 170.

Pressure sensor 182 may measure the pressure in chamber interior 112 during a combustion test. Pressure sensor 182 may include a differential pressure sensor, such as, for example, a diaphragm with a piezoresistive, piezoelectric, and/or capacitive strain gauge. In other implementations, pressure sensor 182 may include another type of pressure sensor, such as an absolute pressure sensor. Pressure sensor cooling jacket 184 may thermally insulate pressure sensor 182 from inner walls 114 in order to ensure that measurements made by pressure sensor 182 are not affected by the elevated temperatures of inner walls 114.

Sample injector 130 may include a pressure injection system for injecting a fuel sample from sample container 132 into chamber interior 112 via sample conduit 134 and sample injector nozzle 136. Pump 133 may pressurize the sample from sample container 132 and pump the sample to sample injector 130. Gas mixer 140 may mix gases from gas cylinders 142 to generate a particular gas mixture, such as a gas mixture with a specified percentage of oxygen, based on instructions received from controller unit 180 and/or based on information received from oxygen sensor 150 and provide the generated gas mixture into chamber interior via gas conduit 144 and gas conduit nozzle 146. For example, gas mixer 140 may be configured to mix nitrogen gas with at least one of air or oxygen gas to generate a gas mixture with a particular percentage of oxygen content using feedback information received from oxygen sensor 150. Furthermore, gas mixer 140 may include a pump configured to raise pressure inside chamber interior 112 to a particular pressure value for a combustion test by pumping a gas mixture into combustion chamber 110. Gas cylinders 142 may include an oxygen ($O_2$) gas cylinder, a nitrogen ($N_2$) gas cylinder, and a purified air gas cylinder. Alternatively, ambient air may be used as an air source.

Cooling system 160 may pump water and/or a cooling fluid through cooling system conduits 162. Cooling system conduits 162 may guide the water and/or cooling fluid to cool sample injector nozzle 136 and/or pressure sensor 182 during a combustion test. In some implementations, pressure sensor 182 may include integrated cooling conduits that may be coupled to cooling system conduits 162 to cool pressure sensor 182 during a combustion test.

Heating controller 170 may be coupled to heating element 118 to provide power to heating element 118 to raise the temperature of chamber interior 112 to a particular temperature during a combustion test. Heating controller 170 may receive information from temperature sensor 172 and/or controller 180 in order to regulate heating element 118 to maintain a particular temperature in chamber interior 112.

Controller unit 180 may include a processor, microcontroller, and/or computer device that controls the operation of constant volume combustion chamber system 100, collects measurements during a combustion test, performs analysis of the measurements, determines a research octane number function for a set of combustion test conditions, and/or determines a research octane number for a fuel sample based on a combustion test. Exemplary components of controller unit 180 are described below with reference to FIGS. 2 and 3. Power supply 190 may supply power to controller unit 180, sample injector 130, gas mixer 140, oxygen sensor 150, cooling system 160, heating controller 170, and/or pressure sensor 182 (connections not shown in FIG. 1).

Although FIG. 1 shows exemplary components of constant volume combustion chamber system 100, in other implementations, constant volume combustion chamber system 100 may include fewer components, different components, differently arranged components, or additional components than depicted in FIG. 1. Additionally, or alternatively, one or more components of constant volume combustion chamber system 100 may perform functions described as being performed by one or more other components of constant volume combustion chamber system 100.

Figure 2:
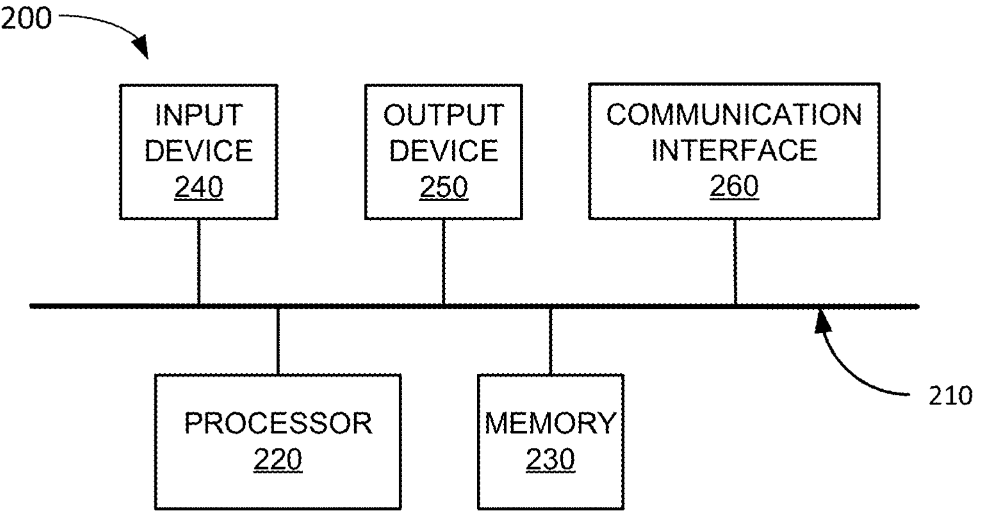
FIG. 2 illustrates exemplary components of a controller unit or other components of a constant volume combustion chamber system according to an implementation described herein.

FIG. 2 is a diagram illustrating example components of device 200 according to an implementation described herein. For example, sample injector 130, gas mixer 140, cooling system 160, heating controller 170, and/or controller unit 180 may each include one or more devices 200. As shown in FIG. 2, device 200 may include a bus 210, a processor 220, a memory 230, an input device 240, an output device 250, and a communication interface 260.

Bus 210 may include a path that permits communication among the components of device 200. Processor 220 may include any type of single-core processor, multi-core processor, microprocessor, latch-based processor, and/or processing logic (or families of processors, microprocessors, and/or processing logics) that interprets and executes instructions. In other embodiments, processor 220 may include an application-specific integrated circuit (ASIC), a field-programmable gate array (FPGA), and/or another type of integrated circuit or processing logic.

Memory 230 may include any type of dynamic storage device that may store information and/or instructions, for execution by processor 220, and/or any type of non-volatile storage device that may store information for use by processor 220. For example, memory 230 may include a random access memory (RAM) or another type of dynamic storage device, a read-only memory (ROM) device or another type of static storage device, a content addressable memory (CAM), a magnetic and/or optical recording memory device and its corresponding drive (e.g., a hard disk drive, optical drive, etc.), and/or a removable form of memory, such as a flash memory.

Input device 240 may allow an operator to input information into device 200. Input device 240 may include, for example, a keyboard, a mouse, a pen, a microphone, a remote control, an audio capture device, an image and/or video capture device, a touch-screen display, and/or another type of input device. In some embodiments, device 200 may be managed remotely and may not include input device 240. In other words, device 200 may be "headless" and may not include a keyboard, for example.

Output device 250 may output information to an operator of device 200. Output device 250 may include a display, a printer, a speaker, and/or another type of output device. For example, device 200 may include a display, which may include a liquid-crystal display (LCD), light emitting diode (LED) display, etc., for displaying content to the operator. In some embodiments, device 200 may be managed remotely and may not include output device 250. In other words, device 200 may be "headless" and may not include a display, for example.

Communication interface 260 may include a transceiver that enables device 200 to communicate with other devices and/or systems via wireless communications (e.g., radio frequency, infrared, and/or visual optics, etc.), wired communications (e.g., conductive wire, twisted pair cable, coaxial cable, transmission line, fiber optic cable, and/or waveguide, etc.), or a combination of wireless and wired communications. Communication interface 260 may include a transmitter that converts baseband signals to radio frequency (RF) signals and/or a receiver that converts RF signals to baseband signals. Communication interface 260 may be coupled to an antenna for transmitting and receiving RF signals.

Communication interface 260 may include a logical component that includes input and/or output ports, input and/or output systems, and/or other input and output components that facilitate the transmission of data to other devices. For example, communication interface 260 may include a network interface card (e.g., Ethernet card) for wired communications and/or a wireless network interface (e.g., a WiFi) card for wireless communications. Communication interface 260 may also include a universal serial bus (USB) port for communications over a cable, a Bluetooth™ wireless interface, a radio-frequency identification (RFID) interface, a near-field communications (NFC) wireless interface, and/or any other type of interface that converts data from one form to another form.

As will be described in detail below, device 200 may perform certain operations relating to performing combustion tests in a constant volume combustion chamber to determine RON functions and using the RON functions to determine RONs for samples. Device 200 may perform these operations in response to processor 220 executing software instructions contained in a computer-readable medium, such as memory 230. A computer-readable medium may be defined as a non-transitory memory device. A memory device may be implemented within a single physical memory device or spread across multiple physical memory devices. The software instructions may be read into memory 230 from another computer-readable medium or from another device. The software instructions contained in memory 230 may cause processor 220 to perform processes described herein. Alternatively, hardwired circuitry may be used in place of, or in combination with, software instructions to implement processes described herein. Thus, implementations described herein are not limited to any specific combination of hardware circuitry and software.

Although FIG. 2 shows exemplary components of device 200, in other implementations, device 200 may include fewer components, different components, additional components, or differently arranged components than depicted in FIG. 2. Additionally, or alternatively, one or more components of device 200 may perform one or more tasks described as being performed by one or more other components of device 200.

Figure 3:
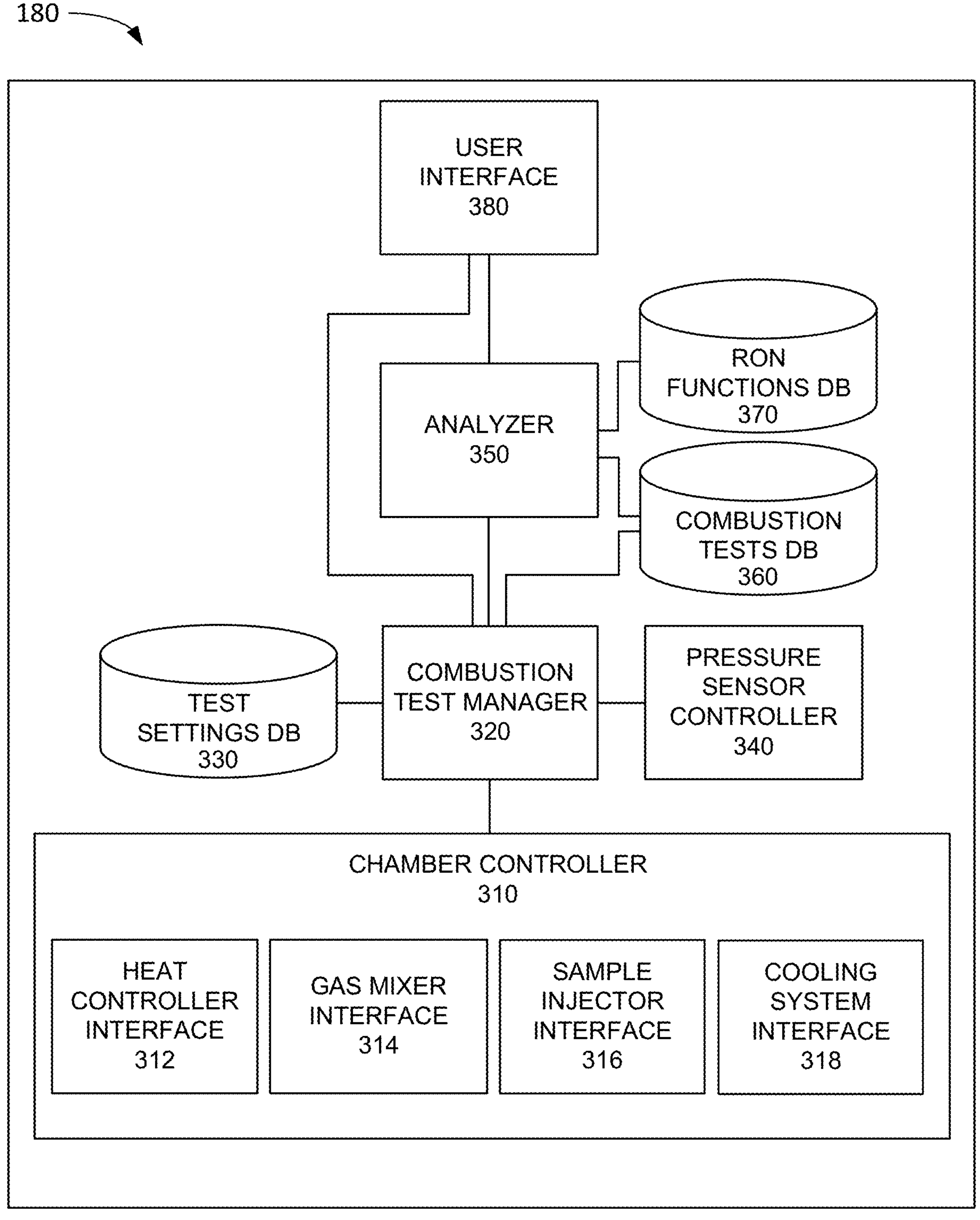
FIG. 3 illustrates exemplary functional components of a controller unit according to an implementation described herein.

FIG. 3 illustrates exemplary functional components of controller unit 180. The functional components of controller unit 180 may be implemented, for example, via processor 220 executing instructions from memory 230. As shown in FIG. 3, controller unit 180 may include a chamber controller 310, a combustion test manager 320, a test settings database (DB) 330, a pressure sensor controller 340, an analyzer 350, a combustion tests DB 360, a RON functions DB 370, and a user interface 380.

Chamber controller 310 may control the operation of constant volume combustion chamber system 100 based on information received from combustion test manager 320. Chamber controller 310 may include a heating controller interface 312, a gas mixer interface 314, a sample injector interface 316, and a cooling system interface 318. Heating controller interface 312 may be configured to interface with heating controller 170. For example, heating controller interface 312 may instruct heating controller 170 to maintain a particular temperature during a combustion test. Gas mixer interface 314 may be configured to interface with gas mixer 140. For example, gas mixer interface 314 may instruct or signal gas mixer 140 to generate a particular gas mixture for a combustion test (e.g., a particular oxygen percentage) and/or generate a particular pressure inside chamber interior 112 for the combustion test. Sample injector interface 316 may be configured to interface with sample injector 130. For example, sample injector interface 316 may instruct sample injector 130 to inject a sample for a particular duration during a combustion test. Cooling system interface 318 may be configured to interface with cooling system 160. For example, cooling system interface 318 may instruct cooling system 160 to start circulating water and/or cooling fluid before, during, and/or after a combustion test.

Combustion test manager 320 may manage combustion tests performed by constant volume combustion chamber system 100. For example, combustion test manager 320 may obtain a combustion test setting from test settings DB 330, perform a combustion test according to the obtained combustion test setting, receive pressure versus time data for the combustion test via pressure sensor controller 340, and store the received pressure versus time data in combustion tests DB 360.

Test settings DB 330 may store information relating to combustion test setting for combustion tests. For example, a combustion test setting may store information identifying a combustion test, a temperature at which to perform the combustion test, a pressure at which to perform the combustion test, an oxygen percentage for a gas mixture at which to perform the combustion test, a fuel injection setting for sample injector 130, a time interval at which to record the pressure during the combustion test, and/or other types of settings that may be selected for the combustion test.

Pressure sensor controller 340 may control pressure sensor 182. For example, pressure sensor controller 340 may activate and/or communicate with pressure sensor 182 and obtain pressure values captured by pressure sensor 182 during a combustion test. Analyzer 350 may analyze data collected and stored in combustion tests DB 360. For example, analyzer 350 may determine a set of pressure parameter values for a sample based on pressure versus time data, such as, for example, values for minimum pressure parameter; a maximum pressure parameter; a maximum pressure rise rate magnitude parameter corresponding to a maximum of the first derivative of pressure; a maximum low temperature pressure rise rate magnitude parameter corresponding to the maximum first derivative of pressure during LTHR; a maximum pressure rise rate point parameter, corresponding to a time at which the first derivative of pressure reaches a maximum level; a low temperature ignition delay parameter, corresponding to a time at which the first derivative of pressure reaches a particular threshold value during LTHR and representing the LTHR start; a high temperature ignition delay, corresponding to a time at which the third derivative of pressure reaches a maximum level before the maximum first derivative of pressure occurs and representing the HTHR start; and/or other types of parameters that may be derived from pressure versus time data.

Analyzer 350 may use the determined pressure parameter values for samples for which RONs are known, together with the known RON values, to generate a RON function for a set of combustion test conditions. Samples for which RONs are known may include, for example, reference samples for which RONs are established and/or samples for which RONs have been determined using another testing system or using another process for determining RONs. Analyzer 350 may correlate a set of pressure parameter values for a sample and the known or previously determined RON for the sample to generate a RON function using regression analysis and/or a machine learning model.

The machine learning model may include a trained deep learning neural network or another type of machine learning classifier, such as, for example, a Support Vector Machine (SVM) classifier, a K-nearest neighbors (KNN) classifier, a naïve B ayesian classifier, a random forest classifier, a logistic regression classifier, a linear discriminant analysis classifier, a quadratic linear discriminant analysis classifier, a maximum entropy classifier, a kernel density estimation classifier, a principal component analysis (PCA) classifier, etc.

Analyzer 350 may generate the RON function using combustion tests for a set of samples with known or previously determined RONs. Alternatively, a RON function may be generated based on a combustion test for a single sample with a known or previously determined RON and then refined with combustion tests for additional samples with known or previously determined RONs. Furthermore, different RON functions may be generated for different sets of test conditions.

Analyzer 350 may then use the generated RON functions to determine RONs for samples for which RONs are unknown or have not been previously determined. For example, analyzer 350 may generate a set of pressure parameter values for a sample based on pressure versus time data obtained during a combustion test for the sample under a set of conditions and use the set of pressure parameter values as inputs to a RON function to generate a RON for the sample.

Combustion tests DB 360 may store information relating to combustion tests performed by constant volume combustion chamber system 100. Exemplary information that may be stored in combustion tests DB 360 is described below with reference to FIG. 4. RON functions DB 370 may store information relating to RON functions generated using constant volume combustion chamber system 100. For example, for each combustion chamber 110 and each set of combustion test conditions (e.g., a particular chamber pressure, chamber temperature, oxygen percentage of gas mixture, sample injection pressure and/or duration, etc.), RON functions DB 370 may store a set of pressure parameter inputs and a RON function used to generate a RON value based on the set of pressure parameter inputs.

User interface 380 may include an interface that enables a user to control constant volume combustion chamber system 100 and/or receive information generate by controller unit 180, such as a generated pressure versus time plot, a plot of a particular pressure parameter derived from pressure versus time data, a generated RON function, a computed RON for a sample, messages regarding a combustion test that has been completed or is in progress, and/or other types of information that may be inputted by a user or that may be outputted for the user. User interface 380 may be configured to interact with input device 240 and/or output device 250.

Although FIG. 3 shows exemplary components of controller unit 180, in other implementations, controller unit 180 may include fewer components, different components, additional components, or differently arranged components than depicted in FIG. 3. Additionally, or alternatively, one or more components of controller unit 180 may perform one or more tasks described as being performed by one or more other components of controller unit 180.

Figure 4:
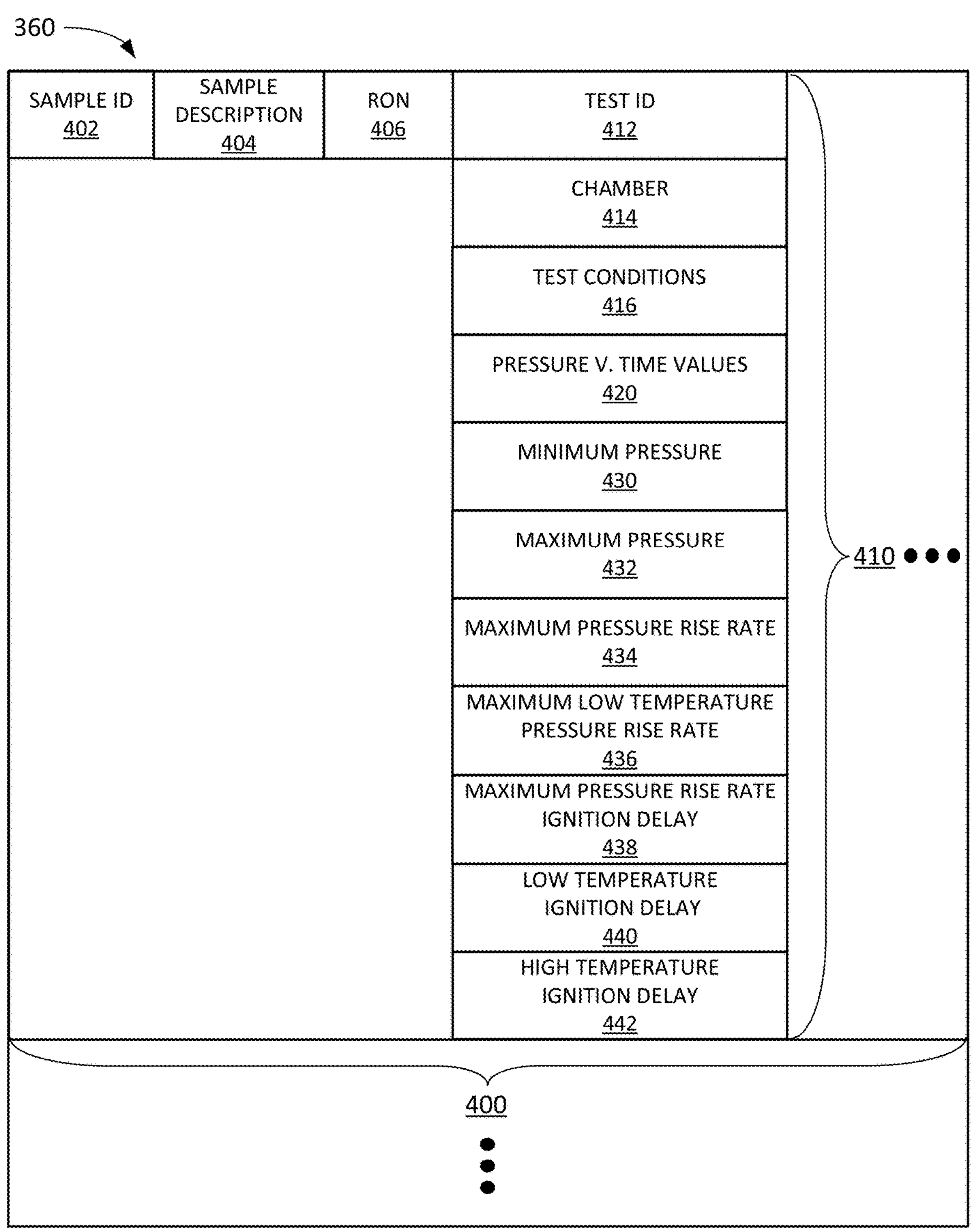
FIG. 4 illustrates exemplary components of a combustion tests database according to an implementation described herein.

FIG. 4 illustrates exemplary components of combustion tests DB 360. As shown in FIG. 4, combustion tests DB 360 may include one or more sample records 400. Each sample record 400 may store information relating to a particular sample. Sample record 400 may include a sample identifier (ID) field 402, a sample description field 404, a RON field 406, and one or more combustion test records 410.

Sample ID field 402 may store an ID for a particular sample. Sample description field 404 may store a description for the particular sample. RON field 406 may store a RON determined for the particular sample. Each combustion test record 410 may store information relating to a particular combustion test performed for the particular sample.

Combustion test record 410 may include a test ID field 412, a chamber field 414, a test conditions field 416, a pressure versus time values field 420, a minimum pressure field 430, a maximum pressure field 432, a maximum pressure rise rate field 434, a maximum low temperature pressure rise rate field 436, a maximum pressure rise rate ignition delay field 438, a low temperature ignition delay field 440, and a high temperature ignition delay field 442.

Test ID field 412 may store an ID for a combustion test. Chamber field 414 may store information identifying combustion chamber 110 used to perform the combustion test. In some implementations, controller unit 180 may be associated with multiple combustion chambers 110 and each combustion chamber 110 may be associated with a separate set of RON functions. For example, different combustion chambers 110 may have different volumes and/or shapes.

Test conditions field 416 may include information identifying test conditions under which the combustion test was performed, such as, for example, a chamber pressure, a chamber temperature, a percentage of oxygen and/or of other gases in a gas mixture used for the combustion test, an amount of the sample used for the combustion test, injection pressure and/or duration, and/or other types of settings that may be selected and applied to a combustion test.

Pressure versus time values field 420 may store a set of pressure values captured by pressure sensor 182 at particular time points during the combustion test. Minimum pressure field 430 may store a minimum pressure value recorded during the combustion test. Maximum pressure field 432 may store a maximum pressure value recorded during the combustion test. Maximum pressure rise rate field 434 may store a maximum pressure rise rate value computed as the maximum of the first derivative of pressure with respect to time. Maximum low temperature pressure rise rate field 436 may store a maximum low temperature pressure rise rate value computed as the maximum of the first derivative of pressure with respect to time during LTHR. Maximum pressure rise rate ignition delay field 438 may store a value for the time at which the maximum pressure rise rate occurs. Low temperature ignition delay field 440 may store a value for the time at which the first derivative of pressure with respect to time reaches a particular threshold value during LTHR and representing the LTHR start. High temperature ignition delay field 442 store a value for the time at which the third derivative of pressure with respect to time reaches a maximum value before the maximum first derivative of pressure with respect to time occurs, representing the HTHR start.

Although FIG. 4 shows exemplary components of combustion tests DB 360, in other implementations, combustion tests DB 360 may include fewer components, different components, additional components, or differently arranged components than depicted in FIG. 4.

Figure 5:
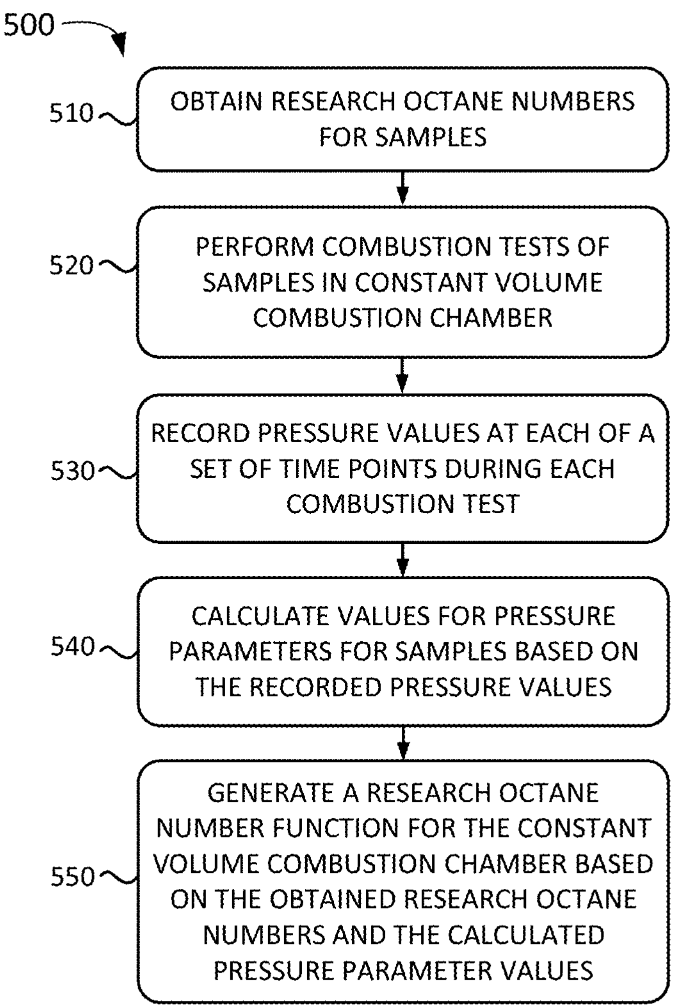
FIG. 5 is a flowchart of a process for determining a research octane number function according to an implementation described herein.

FIG. 5 is a flowchart of a first process 500 for determining a research octane number function according to an implementation described herein. In some implementations, the process of FIG. 5 may be performed by, and/or using, constant volume combustion chamber system 100. In other implementations, some or all of the process of FIG. 5 may be performed by, or using, another device or a group of devices separate from constant volume combustion chamber system 100.

Process 500 may include obtaining RONs for samples (block 510). For example, an operator may enter a known or previously determined RON for a sample into analyzer 350 via user interface 380. For example, the sample may correspond to a reference sample with a well-defined RON, such as a reference sample fuel, or a sample for which a RON has been determined using a different system, such as a CFR engine. A combustion test may then be performed on the sample after the sample is placed in sample container 132.

Process 500 may further include performing combustion tests of samples in a constant volume combustion chamber (block 520) and recording pressure values at each of a set of time points during each combustion test (block 530). For example, controller unit 180 may receive a selection of a set of conditions from an operator, such as a chamber pressure, chamber temperature, gas mixture specification, and/or sample injection pressure and/or duration to use during the combustion test and may perform a combustion test on the sample using the selected set of conditions. Controller unit 180 may receive pressure readings during the combustion test from pressure sensor 182 and may store pressure versus time data for the combustion test in combustion tests DB 360.

Process 500 may further include calculating values for pressure parameters for samples based on the recorded pressure values (block 540). Controller unit 180 may compute the minimum pressure $P_{min}$ representing the pressure decrease during fuel injection. Furthermore, controller unit 180 may compute the maximum pressure $P_{max}$, representing the pressure increase after ignition occurs. Additionally, controller unit 180 may compute a magnitude of the maximum pressure rise rate $$\frac{dP}{dt}_{max}$$

for the sample, corresponding to a maximum of the first derivative of pressure with respect to time (dP/dt). Additionally, controller unit 180 may compute a magnitude of the maximum low temperature pressure rise rate $$\frac{dP}{dt}_{max\ LT}$$

for the sample, corresponding to a maximum value of the first derivative of pressure with respect to time (dP/dt) during LTHR. Additionally, controller unit 180 may compute a maximum pressure rise rate ignition delay value $$ID_{\frac{dP}{dt}max}$$

for the sample, corresponding to a time at which a first derivative of pressure with respect to time (dP/dt) reaches a maximum value. Additionally, controller unit 180 may compute a low temperature ignition delay value $ID_{LT}$ for the sample, corresponding to a time at which a first derivative of pressure with respect to time (dP/dt) reaches a particular threshold value during LTHR, representing the LTHR start. Additionally, controller unit 180 may compute a high temperature ignition delay value ID HT for the sample, corresponding to a time at which a third derivative of pressure with respect to time $$\left(\frac{d^3P}{dt^3}\right)$$

reaches a maximum value before the maximum first derivative of pressure with respect to time (dP/dt) occurs, representing the HTHR start.

Process 500 may further include generating a RON function for the constant volume combustion chamber based on the obtained RONs and the calculated pressure parameter values for samples (block 550). For example, controller unit 180 may determine a function using Equation (1):

$$RON = f\left(P_{min}, P_{max,}, \frac{dP}{dt}_{max}, \frac{dP}{dt}_{max\,LT}, ID_{\frac{dP}{dt}_{max}}, ID_{LT}, ID_{HT}\right) \quad \text{(Eq. 1)}$$

For example, controller unit 180 may correlate the obtained RON value for a particular sample with the set of pressure parameter values computed for the particular sample for each of the samples to generate the RON function. Controller unit 180 may use regression analysis and/or a machine learning model, such as a deep learning neural network, an SVM classifier, a KNN classifier, a naïve Bayesian classifier, a random forest classifier, a logistic regression classifier, a linear discriminant analysis classifier, a quadratic linear discriminant analysis classifier, a maximum entropy classifier, a kernel density estimation classifier, a principal component analysis (PCA) classifier, and/or another type of classifier to generate the RON function.

Figure 6:
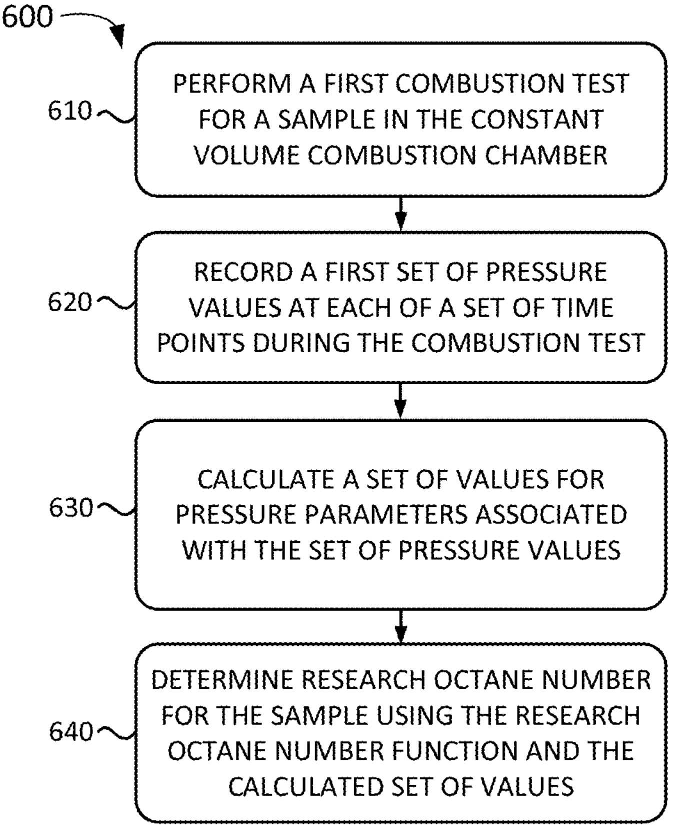
FIG. 6 is a flowchart of a process for determining a research octane number based on a research octane number function according to an implementation described herein.

FIG. 6 is a flowchart of a process for determining a research octane number based on a research octane number function according to an implementation described herein. In some implementations, the process of FIG. 6 may be performed by, and/or using, constant volume combustion chamber system 100. In other implementations, some or all of the process of FIG. 6 may be performed by, or using, another device or a group of devices separate from constant volume combustion chamber system 100.

Process 600 may include performing a combustion test for a sample in the constant volume combustion chamber (block 610), recording a set of pressure values at each of a set of time points during the combustion test (block 620), and calculating a set of values for pressure parameters associated with the research octane number function based on the set of pressure values (block 630). For example, controller unit 180 may perform a combustion test on a sample, obtain a set of pressure versus time data for the combustion test (e.g., data associated with combustion test records 410 described above), and generate a set of values for a set of pressure parameters for the combustion test based on the obtained set of pressure versus time data (e.g., one or more values in combustion test records 410 described above).

Process 600 may further include determining a research octane number for the sample using the RON function and the set of pressure parameter values (block 640). For example, controller unit 180 may use Equation (1) (described above) to compute a RON value for the sample using the generated set of pressure parameter values as inputs into the RON function.

Figure 7:
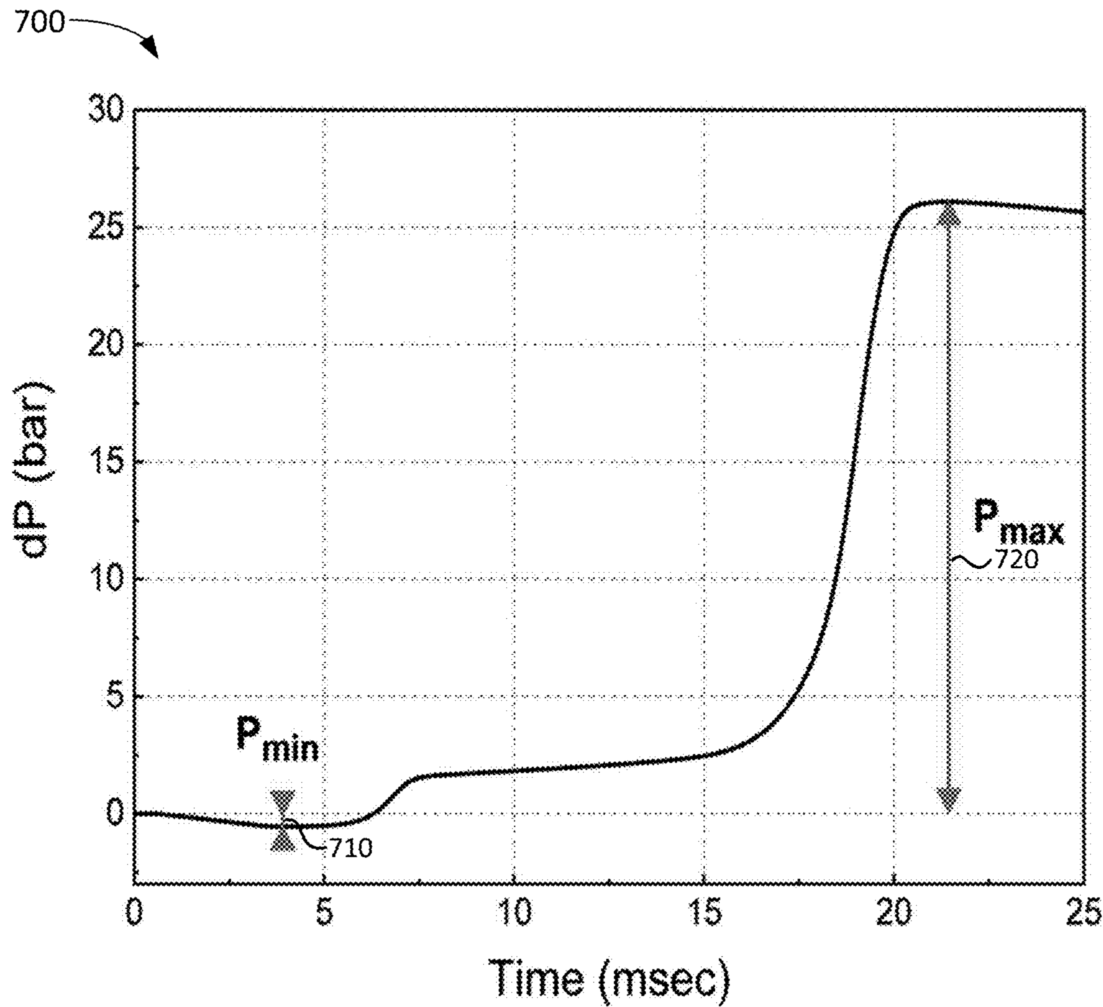
FIG. 7 illustrates an exemplary plot of pressure versus time data according to an implementation described herein.

FIG. 7 illustrates an exemplary plot 700 of pressure versus time data according to an implementation described herein. As shown in FIG. 7, plot 700 illustrates a plot of pressure versus time data obtained during a combustion test for a sample using constant volume combustion chamber system 100. Plot 700 illustrates an initial pressure drop 710 during sample injection, corresponding to $P_{min}$, and a subsequent pressure increase 720 after ignition of the sample, corresponding to $P_{max}$.

Figure 8:
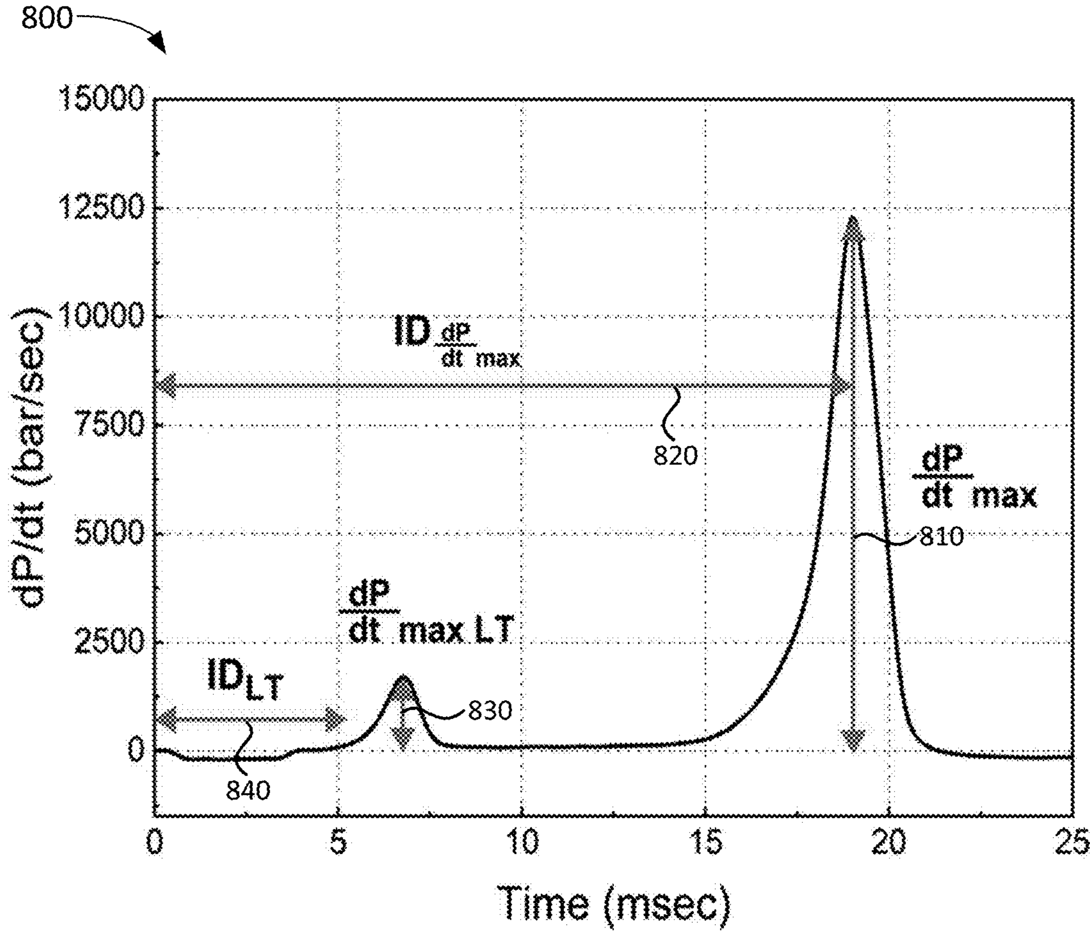
FIG. 8 illustrates an exemplary plot of the first derivative of pressure versus time data according to an implementation described herein.

FIG. 8 illustrates an exemplary plot 800 of pressure rise rate versus time data according to an implementation described herein. As shown in FIG. 8, plot 800 illustrates a plot of the first derivative of pressure versus time generated based on the pressure versus time data of FIG. 7. The pressure rise rate, measured in bar/second, corresponds to the first derivative of pressure with respect to time (dP/dt). Plot 800 illustrates the maximum pressure rise rate 810 corresponding to the maximum (dP/dt) value and further illustrates $$ID_{\frac{dP}{dt}_{max}}$$

820, the time at which the maximum (dP/dt) value occurs. Furthermore, plot 800 illustrates a magnitude of the maximum low temperature pressure rise rate $$\frac{dP}{dt}_{max\,LT}$$

830 for the sample, corresponding to a maximum value of the first derivative of pressure with respect to time (dP/dt) during LTHR, and a low temperature ignition delay value $ID_{LT}$ 840 for the sample, corresponding to a time at which a first derivative of pressure with respect to time (dP/dt) reaches a particular threshold value during LTHR, and representing the LTHR start.

Figure 9:
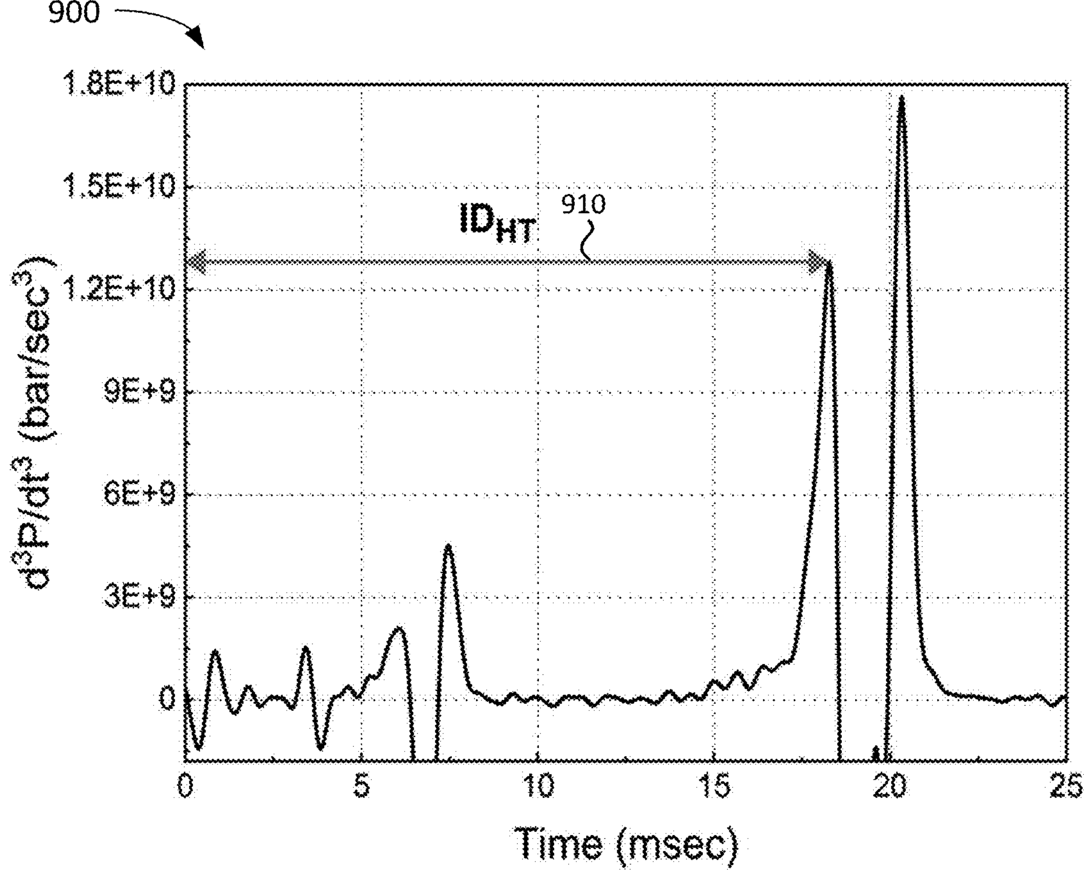
FIG. 9 illustrates an exemplary plot of the third derivative of pressure versus time data according to an implementation described herein.

FIG. 9 illustrates an exemplary plot 900 of the third derivative of pressure versus time data according to an implementation described herein. As shown in FIG. 9, plot 900 illustrates a plot of the third derivative of pressure with respect to time $$\left(\frac{d^3P}{dt^3}\right)$$

generated based on the pressure versus time data of FIG. 7. Plot 900 further illustrates the high temperature ignition delay value $ID_{HT}$ 910, corresponding to a time at which a third derivative of pressure with respect to time $$\left(\frac{d^3P}{dt^3}\right)$$

reaches a maximum value before the maximum first derivative of pressure occurs.

This application incorporates by reference the following application: U.S. Provisional Patent Application Serial. No. 63/380,034, filed on Oct. 18, 2022, titled "Prediction of Motor Octane Number Using a Constant Volume Combustion Chamber."

In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

For example, while series of blocks have been described with respect to FIGS. 5 and 6, the order of the blocks may be modified in other implementations. Further, non-dependent blocks and/or signals may be performed in parallel.

It will be apparent that systems and/or methods, as described above, may be implemented in many different forms of software, firmware, and hardware in the implementations illustrated in the figures. The actual software code or specialized control hardware used to implement these systems and methods is not limiting of the embodiments. Thus, the operation and behavior of the systems and methods were described without reference to the specific software code—it being understood that software and control hardware can be designed to implement the systems and methods based on the description herein.

Further, certain portions, described above, may be implemented as a component that performs one or more functions. A component, as used herein, may include hardware, such as a processor, an ASIC, or a FPGA, or a combination of hardware and software (e.g., a processor executing software).

It should be emphasized that the terms "comprises"/"comprising" when used in this specification are taken to specify the presence of stated features, integers, steps or components but does not preclude the presence or addition of one or more other features, integers, steps, components or groups thereof.

The term "logic," as used herein, may refer to a combination of one or more processors configured to execute instructions stored in one or more memory devices, may refer to hardwired circuitry, and/or may refer to a combination thereof. Furthermore, a logic may be included in a single device or may be distributed across multiple, and possibly remote, devices.

For the purposes of describing and defining the present invention, it is additionally noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

No element, act, or instruction used in the present application should be construed as critical or essential to the embodiments unless explicitly described as such. Also, as used herein, the article "a" is intended to include one or more items. Further, the phrase "based on" is intended to mean "based, at least in part, on" unless explicitly stated otherwise.

What is claimed is:

1. A method comprising:

obtaining a research octane number for a sample;

performing a combustion test for the sample in a constant volume combustion chamber;

recording, at a plurality of time points during the combustion test, a plurality of pressure values associated with the sample;

calculating one or more values for one or more pressure parameters for the sample based on the plurality of pressure values and the plurality of time points;

generating a research octane number mathematical function for the constant volume combustion chamber based on the obtained research octane number and the calculated one or more values for the one or more pressure parameters; and using the generated research octane number mathematical function to determine a research octane number for a second sample, wherein using the generated research octane number mathematical function to determine a research octane number for the second sample includes:

performing a combustion test for the second sample in the constant volume combustion chamber, calculating a second set of one or more values for the one or more pressure parameters for the second sample based on the combustion test performed for the second sample, and determining a research octane number for the second sample based on the generated research octane number mathematical function and the calculated second set of one or more values for the one or more pressure parameters for the second sample.

2. The method of claim 1, wherein performing the combustion test for the sample in the constant volume combustion chamber includes:

mixing nitrogen gas with at least one of air or oxygen gas to generate a gas mixture with a particular percentage of oxygen content using information received from an oxygen sensor; and injecting the gas mixture into the constant volume combustion chamber.

3. The method of claim 1, wherein the one or more pressure parameters include a low temperature ignition delay parameter corresponding to a time at which a first derivative of pressure reaches a particular threshold value during a low temperature heat release period.

4. The method of claim 1, wherein the one or more pressure parameters include a high temperature ignition delay parameter corresponding to a time at which a third derivative of pressure reaches a maximum value before a maximum first derivative of pressure occurs.

5. The method of claim 1, wherein the one or more pressure parameters include a maximum pressure rise rate ignition delay parameter corresponding to a time at which a first derivative of pressure reaches a maximum value.

6. The method of claim 1, wherein the one or more pressure parameters include a maximum pressure rise rate parameter corresponding to a maximum value of a first derivative of pressure.

7. The method of claim 1, wherein the one or more pressure parameters include a maximum low temperature pressure rise rate parameter corresponding to a maximum value of a first derivative of pressure during a low temperature heat release period of the combustion test.

8. The method of claim 1, wherein the one or more pressure parameters include at least one of a maximum pressure parameter or a minimum pressure parameter.

9. A device comprising:

a memory storing instructions; and a processor configured to execute the instructions to:

obtain a research octane number for a sample;

perform a combustion test for the sample in a constant volume combustion chamber;

record, at a plurality of time points during the combustion test, a plurality of pressure values;

calculate one or more values for one or more pressure parameters for the sample based on the plurality of pressure values and the plurality of time points;

generate a research octane number mathematical function for the constant volume combustion chamber based on the determined research octane number and the calculated one or more values for the one or more pressure parameters; and use the generated research octane number mathematical function to determine a research octane number for a second sample, wherein, when using the generated research octane number mathematical function to determine a research octane number for the second sample, the processor is further configured to:

perform a combustion test for the second sample in the constant volume combustion chamber, calculate a second set of one or more values for the one or more pressure parameters for the second sample based on the combustion test performed for the second sample, and determine a research octane number for the second sample based on the generated research octane number mathematical function and the calculated second set of one or more values for the one or more pressure parameters for the second sample.

10. The device of claim 9, wherein, when performing the combustion test for the sample in the constant volume combustion chamber, the processor is further configured to:

signal a gas mixer to:

mix nitrogen gas with at least one of air or oxygen gas to generate a gas mixture with a particular percentage of oxygen content using information received from an oxygen sensor; and inject the gas mixture into the constant volume combustion chamber.

11. The device of claim 9, wherein the one or more pressure parameters include a low temperature ignition delay parameter corresponding to a time at which a first derivative of pressure reaches a particular threshold value during a low temperature heat release period.

12. The device of claim 9, wherein the one or more pressure parameters include a high temperature ignition delay parameter corresponding to a time at which a third derivative of pressure reaches a maximum value before a maximum first derivative of pressure occurs.

13. The device of claim 9, wherein the one or more pressure parameters include a maximum pressure rise rate ignition delay parameter corresponding to a time at which a first derivative of pressure reaches a maximum value.

14. The device of claim 9, wherein the one or more pressure parameters include a maximum pressure rise rate parameter corresponding to a maximum value of a first derivative of pressure.

15. The device of claim 9, wherein the one or more pressure parameters include a maximum low temperature pressure rise rate parameter corresponding to a maximum value of a first derivative of pressure during a low temperature heat release period of the combustion test.

16. A system comprising:

a constant volume combustion chamber comprising:

a pressure sensor configured to record a pressure inside the constant volume combustion chamber, wherein the pressure sensor includes a cooling jacket; and a controller configured to:

perform a combustion test for a sample in the constant volume combustion chamber;

record, at a plurality of time points during the combustion test, a plurality of pressure values using the pressure sensor;

calculate one or more values for one or more pressure parameters based on the recorded plurality of pressure values; and determine a research octane number for the sample using a research octane number mathematical function and the calculated one or more values for the one or more pressure parameters.

17. The system of claim 16, wherein the constant volume combustion chamber further includes:

a gas injector to inject a gas mixture into the constant volume combustion chamber.

18. The system of claim 17, wherein the constant volume combustion chamber further includes:

a gas mixer comprising an oxygen sensor, wherein the gas mixer is configured to:

mix nitrogen gas with at least one of air or oxygen gas to generate the gas mixture with a particular percentage of oxygen content using information received from the oxygen sensor; and provide the gas mixture to the gas injector.

19. The method of claim 1, wherein the one or more pressure parameters includes at least one parameter based on a derivative of pressure with respect to time.

20. The device of claim 9, wherein the one or more pressure parameters includes at least one parameter based on a derivative of pressure with respect to time.

* * * * *